United States Patent [19]
Garay et al.

[11] Patent Number: 5,626,878
[45] Date of Patent: May 6, 1997

[54] REDUCTION OF ELECTROSTATIC FORCES BETWEEN MAGNESIUM TRISILICATE ADSORBATES

[75] Inventors: Felipe Garay, Ogdensburg; Stanley Lech, Rockaway, both of N.J.; Mark Oehling, East Stroudsburg, Pa.

[73] Assignee: Warner Lambert Company, Morris Plains, N.J.

[21] Appl. No.: 370,927

[22] Filed: Jan. 10, 1995

[51] Int. Cl.$^6$ .................... A61K 9/18; A61K 9/20
[52] U.S. Cl. .................. 424/489; 424/439; 424/464; 514/770; 514/774; 514/778; 514/781; 514/949; 514/951; 514/961; 514/974
[58] Field of Search .................. 424/439, 440, 424/441, 489, 464; 514/770, 949, 951, 961, 974

[56] References Cited

U.S. PATENT DOCUMENTS

| | | | |
|---|---|---|---|
| 3,085,942 | 4/1963 | Magid | 167/67 |
| 4,581,232 | 4/1986 | Peters et al. | 424/155 |
| 4,642,231 | 2/1987 | Peters et al. | 424/15 |
| 4,647,459 | 3/1987 | Peters et al. | 424/155 |
| 4,753,800 | 6/1988 | Mozda | 424/440 |
| 4,758,424 | 7/1988 | Denick, Jr. et al. | 424/48 |
| 4,761,274 | 8/1988 | Denick, Jr. et al. | 424/48 |

FOREIGN PATENT DOCUMENTS

| | | |
|---|---|---|
| 0132472 | 2/1985 | European Pat. Off. . |
| 0587137 | 3/1994 | European Pat. Off. . |
| WO9420074 | 9/1994 | WIPO . |
| WO9503785 | 2/1995 | WIPO . |

OTHER PUBLICATIONS

Prof. Dr.rer.nat.habil. Rudolf Voigt and r.rer.nat. Manfred Borschein (1975). Lehrbuch de pharmazeutischen Technologie. Mit 263 Abbildungen und 111 Tabellen, pp. 157–160.

*Primary Examiner*—James M. Spear
*Attorney, Agent, or Firm*—Michael J. Atkins

[57] ABSTRACT

A medicament adsorbate containing corn syrup having contained therein from about 10 to about 90% by weight of the adsorbate of a medicament drug a magnesium trisilicate having a surface area of at least 400 m$^2$/g and having a structure with multiple interstitial spaces, and having adsorbed therein from about 0.5 to about 30% by weight of the adsorbate of a medicament drug, wherein the medicament drug is an antihistamine. A reduction in the electrostatic forces between adsorbates is experienced due to the particle size of the adsorbate being in the range greater than 40 to about 800 um, most of the adsorbates prepared being a particle size greater than 150 um, which allows for better processing.

24 Claims, No Drawings

1

REDUCTION OF ELECTROSTATIC FORCES BETWEEN MAGNESIUM TRISILICATE ADSORBATES

FIELD OF THE INVENTION

This invention pertains to magnesium trisilicate adsorbates of an increased particle size. The size of the adsorbates decreases the electrostatic forces which seek to bring together the particles and improves the processing of the adsorbates into pharmaceutical compositions.

BACKGROUND OF THE INVENTION

In the development of oral formulations many factors must be considered. They include: (1) the drug should be stable in the presence of formulation excipients; (2) the drug should be recovered from the formulation excipients; (3) the drug should exhibit acceptable dissolution characteristics from the formulation; (4) processing should allow for acceptable content uniformity; and (5) the formulation should have acceptable physical characteristics. Many of these aspects are addressed in preformulation through drug-excipient compatibility studies. Chemical stability is often the primary concern with drug-excipient compatibility evaluations.

The drug-excipient physical interactions, however, can also affect the formulation performance and the development of analytical methodology. For instance, although the interactions resulting in the adsorption of drugs onto solid dosage form excipients are generally of a weak type such as Van der Waals forces and hydrogen bonding, they have been shown to influence and affect content uniformity of solid dosage forms.

For example, in the manufacture of tablets, segregation of medicament adsorbates of a small particle size from solid dosage form excipients can occur due to the electrostatic nature of the adsorbates. Once the adsorbates segregate, they re-agglomerate into tiny spheres which are high in drug concentration. This is visually evident and can be observed in the blend uniformity and solid dosage form uniformity. The segregation of medicament adsorbates of a small particle size, therefore, contributes to variation in the drug content of solid dosage forms such as tablets which is unfavorable due to the unreliable delivery of a medicament.

An example of a medicament adsorbate which has demonstrated the unfavorable drug-excipient physical interactions are those which are prepared from magnesium trisilicates. The adsorption of a medicament onto magnesium trisilicates in the preparation of a medicament adsorbate has been taught in the literature as a method to render bitter drug principles tasteless in liquid, tablet and chewable dosage forms which become readily bioavailable when the adsorbate reaches the low pH acid media of the stomach. Unfortunately, the resulting adsorbate formed has a very smart particle size (30 microns) and is very electrostatic. As indicated above, these electrostatic forces cause the adsorbate to segregate from the excipients and re-agglomerate into tiny spheres which are high in drug concentration. Solid dosage forms prepared with the medicament adsorbates vary by ten percent or more in their drug concentration due to the lack of blend uniformity.

It can be understood that it would be an improvement to the art if one could reduce the electrostatic properties of the adsorbate without effecting taste masking. Reduction of the electrostatic forces would improve the processing of adsorbates such as those containing magnesium trisilicate and provide for a more uniform composition.

U.S. Pat. No. 3,085,942 to Magid discloses the formation of an antitussive composition using dextromethorphan hydrobromide and its acid addition salts adsorbed, in part, on magnesium trisilicate. Magid notes that particle size of the magnesium trisilicate is not critical in preparing the adsorbates and that average particle sizes of about 0.1 to about 150 microns are usable. Magid also notes that when the ingredients are intimately mixed, the bitter taste associated with dextromethorphan is reduced or eliminated. The adsorbate may be mixed with other ingredients to form compressed tablets, candy lozenges, chewing gum tablets and the like.

U.S. Pat. No. 4,581,232 to Peters et al. discloses a medicament adsorbate containing a magnesium trisilicate having a surface area of at least 400 $m^2/g$ and having a flake-like structure with multiple interstitial spaces, and having adsorbed therein from about 1% to about 20% by weight of the adsorbate of a medicament drug, wherein the medicament drug is an antitussive such as dextromethorphan hydrobromide. This patent further discloses that the adsorbate may be formulated with pharmaceutically acceptable carriers, i.e. diluents, binders and adhesives, lubricants, disintegrants, colorants, flavorings, sweeteners, to prepare medicated compositions which offer a variety of textures to suit particular applications. Such compositions may be in the form of a lozenge, tablet, toffee, nougat, chewy candy, chewing gum, and so forth.

U.S. Pat. No. 4,647,459 to Peters et al. discloses a confectionery composition containing a magnesium trisilicate having a surface area of at least 400 $m^2/g$ and having a flake-like structure with multiple interstitial spaces, and having adsorbed therein from about 1% to about 20% by weight of the adsorbate of a medicament drug. Such compositions may be in the form of a lozenge, tablet, toffee, nougat, chewy candy, and so forth.

The U.S. patents discussed herein are expressly incorporated by reference.

SUMMARY OF THE INVENTION

It has been unexpectedly discovered that by using a binder, such a corn syrup, one can increase the particle size and reduce the electrostatic forces of magnesium trisilicate adsorbates without effecting taste masking. In particular, it has been determined that unexpected results are exhibited by a medicament adsorbate comprising from about 0.5% to about 60%, a binder having contained therein from about 10 to about 90% by weight of the adsorbate of a magnesium trisilicate having a surface area of at least 400 $m^2/g$ and having a flake-like structure with multiple interstitial spaces, and having adsorbed therein from about 0.5 to about 30% by weight of the adsorbate of a medicament drug. This particular magnesium trisilicate adsorbate has been found to be suitable for the preparation of uniformly blended tasteless medicament adsorbates.

We have also unexpectedly discovered a process for preparing the medicament adsorbate which process involves dissolving the medicament drug in a solvent, admixing magnesium trisilicate and a binder so as to achieve a homogenous mass, and recovering the medicament adsorbate product. In particular, a process has been discovered which involves dissolving a medicament drug such as diphenhydramine hydrochloride or dextromethorphan hydrobromide in a solvent, admixing magnesium trisilicate having a surface area of at least 400 $m^2/g$ and having a flake-like structure with multiple interstitial spaces along with a binder such as corn syrup so as to achieve a homogenous mass, and recovering the medicament adsorbate product by a drying process.

The medicament adsorbate of the invention may further include a pharmaceutically acceptable carrier and be in the form of a lozenge, tablet, toffee, nougat, chewy candy, and chewing gum.

DETAILED DESCRIPTION OF THE INVENTION

In the preferred embodiment of the present invention, the magnesium trisilicate is a fine, white odorless powder free from grittiness having a surface area of at least 400 $m^2/g$, and preferably at least 400 $m^2/g$ to about 1000 $m^2/g$ and most preferably from about 440 $m^2/g$ to about 600 $m^2/g$ which has a flake-like structure with multiple interstitial spaces.

Nevertheless, in other embodiments of the present invention, normally available magnesium trisilicate may be employed. The term magnesium trisilicate does not have a precise description but approximates the formula $2MgO_3SiO_2 \times H_2O$. The physical texture and absorptive properties of magnesium trisilicates have been heretofore varied depending predominately upon their mode of preparation. These materials, however, generally possess a water content of 17 to 34%, a minimum of 20% magnesium oxide, a minimum of 45% silicon dioxide, and a ratio of MgO to $SiO_2$ of about 2.10 to about 2.30.

The normal magnesium trisilicates has a surface area of less than 400 $m^2/g$ and preferably less than 250 $m^2/g$. These materials likewise are globular semi-spherical structures which are non-flake in appearance and are void of interstitial spaces.

The method of making the magnesium trisilicates used in this invention is not critical and is not considered a part of this invention. Magnesium trisilicates of this invention are believed to occur naturally or may be prepared by standard techniques well known to the ordinary skilled artisan which would not involve undue experimentation. Such techniques generally use normal reactants, such as sodium silicate and magnesium sulfate which are reacted under heat, the magnesium trisilicate is precipitated and recovered. See for example U.S. Pat. No. 3,272,594 which is incorporated herein by reference.

The weight percent of the magnesium trisilicate, based on the weight of the adsorbate is from about 10 to about 90%, more preferably about 30 to about 80%, and most preferably about 40 to about 70%.

The medicament drugs used herein may be selected from a wide variety of drugs and their acid addition salts. Both organic and inorganic salts may be used provided the drug maintains its medicament value and is soluble in the solvent. Exemplary acid salts include hydrochloride, hydrobromide, orthophosphate, benzoate, maleate, tartrate, succinate, citrate, salicylate, sulfate, and acetate.

The weight percent of the drug or its acid addition salt thereof, based on the weight of the adsorbate is from about 0.5 to about 30%, more preferably about 5 to about 20%, and most preferably about 8 to about 12%, which amounts will vary depending upon the therapeutic dosage permitted.

Suitable categories of drugs that may be employed in the instant adsorbate may vary widely and generally represent any stable adsorbate drug combination. Illustrative categories and specific examples include:

a) antitussives, such as dextromethorphan, dextromethorphan hydrobromide, noscapine, carbetapentane citrate, and chlophedianol hydrochloride;

b) antihistamines, such as chlorpheniramine maleate, phenindamine tartrate, pyrilamine maleate, doxylamine succinate, phenyltoloxamine citrate, diphenhydramine hydrochloride, promethazine and triprolidine;

c) decongestants, such as phenylephrine hydrochloride, phenylpropanolamine hydrochloride, pseudoephedrine hydrochloride, ephedrine; and d) various alkaloids, such as codeine phosphate, codeine sulfate and morphine.

These materials may be used alone or in combination on the adsorbate within the ranges specified above.

A particularly effective medicament adsorbate has been prepared using dextrmethorphan hydrobromide and/or diphenhydramine hydrochloride.

The binding agents (binders) of the present invention are compounds which exert a strong physicochemical attractive force between molecules. Suitable binding agents in the present invention include corn syrup, starch, sugar, sugar alcohols, polyvinyl pyrrolidine, acacia, gelatin, glucose, guar gum, pregelatinized starch and sodium alginate, and cellulose derivatives such as ethylcellulose, hydroxypropylcellulose, hydroxypropylmethylcellulose, methylcellulose, sodium carboxymethylcellulose, and the like, and mixtures thereof. Preferably, the binding agent is corn syrup.

Corn syrup is essentially liquid glucose and can be in liquid or solid form. One commercially available corn syrup is EMDEX® which is manufactured by Mendell Company.

EMDEX® is a highly refined product composed almost entirely of free-flowing spray crystallized porous spheres. For optimum performance, it requires a lubricant such as magnesium stearate, used in the proportion of 0.5 to 1% based on the weight of the formulation. Although the composition of EMDEX® is well-known in the art, the typical chemical composition comprises the following carbohydrates: dextrose (95%), isomaltose (2.0%), maltotriose (less than 0.1%), maltose (1.0%), gentiobiose (2.0%), and panose (less than 0.5%). Whereas EMDEX® is the preferred binding agent, it should be understood that other binders can be employed which reduce the electrostatic forces between magnesium trisilicate adsorbates such that an adsorbate can be prepared which exhibits the properties or characteristics discussed herein.

The amount of binding agent in the adsorbate is an effective amount to reduce the electrostatic forces between magnesium trisilicate adsorbates. An effective amount of binding agent is an amount which will allow a medicament adsorbate to be uniformly distributed throughout a medical product. The amount of binding agent is a matter of preference, subject to such factors as the type of magnesium trisilicate or medicament, type and amount of binder employed, and the other ingredients in the drug delivery system. Thus, the amount of binding agent may be varied in order to obtain the result desired in the final product. In general, the binding agent will be present in an amount from about 0.5 to about 60%, and preferably from about 3 to about 40%, and more preferably from about 10 to about 25%, by weight of the medicament adsorbate.

While the invention is not to be limited to theoretical considerations, it is believed that the use of the binder increases the particle size of the medicament adsorbate. The increased particle size of the medicament adsorbate renders it less susceptible to segregation by added solid dosage form excipients due to the reduction in the electrostatic forces between each medicament adsorbate.

The particle size of medicament adsorbates containing magnesium trisilicate prior to the date of the present invention were on the order of 0.1 to 40 um. The particle size of the medicament adsorbate of the present invention, however, is greater than 40 um. Preferably, the particle size of the medicament adsorbate is in the range greater than 40 to about 800 um. More preferably, the particle size of the medicament adsorbate is in the range from about 150 to about 600 um.

There are additional physical properties of the medicament adsorbates of the present invention that can be characterized and used to differentiate them from adsorbates previously known in the art, such as density and moisture. Adsorbates yielded by previously known techniques were characterized by a density of about 200–500 grams/liter verses medicament adsorbates yielded by the present invention (directly admixing a binding agent with a medicament drug dissolved in solvent and admixed with magnesium trisilicate) achieving a density of about 700–1000 grams/liter. The known adsorbate also dries in about 15 to 18 hours due to the very fine particles which pack down in an oven preventing adequate air flow and uniform drying, as opposed to the medicaments adsorbates of the present invention which dry in about 8 to 12 hours.

It is also been discovered that the medicament adsorbates of the present invention have a desirable dissolution rate profile. More specifically, it has been found that the medicament adsorbates of the present invention have a more rapid release rate of an active drug than previously known adsorbates. Further discussion of this property is provided below in the Example section.

The medicament adsorbate of the invention can be prepared by conventional granulation and or slurry techniques. Both processes involve the initial step of dissolving the medicament drug in a suitable inert solvent and then mixing with the magnesium trisilicate and the binding agent. Concentrations of the drug in solvent may vary widely but are generally from about 10 to about 70% by weight of the total composition. When mixing is performed with low amounts of solvent, for example about 15 to about 35% by weight of the total composition, the resulting granulated product is removed and dried to a predetermined moisture content between about 4 and about 12% by weight of the final composition. When higher solvent concentrations are employed a slurry is formed containing the drug, magnesium trisilicate and binding agent. Concentrations of the drug in solvent may range from about 40 to about 80% by weight of the total composition for optimum results. The solvent is then removed and the adsorbate recovered and used as a paste or dried to a free flowing powder.

Any solvent may be used in the inventive process to prepare the adsorbate providing it is capable of dissolving the medicament drug. Representative solvents include water; polyhalogenated lower hydrocarbons such as chloroform, methylene chloride; lower alcohols, such as methanol, ethanol, propanol and butanol; and aromatic solvents such as benzene, with water being the preferred solvent.

The concentration of magnesium trisilicate added to the solvent may vary widely but is generally from about 30 to about 90% by weight of the total composition. More preferably, the concentration of magnesium trisilicate added to the solvent is from about 50 to about 80% by weight of the total composition. Most preferably, the concentration of magnesium trisilicate added to the solvent is from about 60 to about 80% by weight of the total composition.

The concentration of binder added to the solvent may vary widely but is generally from about 1 to about 90% by weight of the total composition. More preferably, the concentration of binder added to the solvent is from about 20 to about 70% by weight of the total composition. Most preferably, the concentration of binder added to the solvent is from about 20 to about 50% by weight of the total composition.

The medicament adsorbate once prepared may be stored for future use or formulated with conventional additives, that are pharmaceutically acceptable carriers, to prepare medicated compositions which offer a variety of textures to suit particular applications. Such compositions may be in the form of a lozenge, tablet, toffee, nougat, chewy candy, chewing gum, and so forth. The pharmaceutically acceptable carriers may be selected from a wide range of materials. Without being limited thereto, such materials include diluents, binders and adhesives, lubricants, disintegrants, colorants, flavorings, sweeteners and miscellaneous materials such as buffers and adsorbents in order to prepare a particular medicated composition. The preparation of confectionery and chewing gum products is historically well known and has changed very little over the years.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to 1.5% moisture. Such materials normally contain up to 92% corn syrup, up to 55% sugar and from 0.1% to 5.0% water. The syrup component generally is prepared from corn syrups high in fructose, but may include other materials. Further ingredients such as flavorings, sweeteners, acidulents, colorants and so forth may also be added. In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7 g/cc.

By comparison, the high boiling syrup, or "bob syrup", is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND Confectionery:* Science and Technology, 2nd edition, AVI Publishing Co., Inc., Westport, Conn., (1980), at Pages 424–425.

Pharmaceutical tablets of this invention may also be in the form of chewable forms. This form is particularly advantageous because of convenience and patient acceptance and rapid onset of bioactivity. To achieve acceptable stability and quality as well as good taste and mouth feel several considerations are important, namely amount of active substance per tablet, flavor, compressibility and organoleptic properties of the drug.

The preparation of chewable medicated candy is prepared by procedures similar to those used to make soft confectionery. This procedure generally involves the formation of a boiled sugar-corn syrup blend to which is added a frappe mixture. The boiled sugar-corn syrup blend may be prepared from sugar and corn syrup blended in parts by weight ratio of 90 to 10:10 to 90. This blend is heated to temperatures above 250° F. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 150° F. and 250° F. The medicament adsorbate can then be added as the temperature of the mix is lowered to around 150° F. to 200° F. whereupon additional ingredients are added such as flavors, and colorants. The formulation is further cooled and formed to pieces of desired dimensions.

A general discussion of the lozenge and chewable tablet forms of confectionery may be found in H. A. Lieberman and L. Lachman, *Pharmaceutical Dosage Forms: Tablets* Volume I, Marcel Dekker, Inc., New York, N.Y. at pages 289 to 466.

With regard to the chewing gum formulation in particular, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferable about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethene waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfam-K and the like, and the free acid form of saccharin.

C. Dipeptide based sweeteners such as L-aspartyl-phenylalanine methyl ester and materials described in U.S. Pat. No. 3,492,131 and the like.

In general, the amount of sweetener will vary with the desired amount of sweeteners selected for a particular chewing gum. This amount will normally be 0.001% to about 90% by weight when using an easily extractable sweetener. The water-soluble sweeteners described in category A above, are preferably used in amounts of about 25% to about 75% by weight, and most preferably from about 50% to about 65% by weight of the final chewing gum composition. In contrast, the artificial sweeteners described in categories B and C are used in amounts of about 0.005% to about 5.0% and most preferably about 0.05% to about 2.5% by weight of the final chewing gum composition. These amounts are ordinarily necessary to achieve a desired level of sweetness independent from the flavor level achieved from flavor oils. While water may be added independently with dry sweeteners, it will generally be added as part of a corn syrup or corn syrup mixture.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition weight.

The colorants useful in the present invention, include the pigments such as titanium dioxide, that may be incorporated in amounts of up to about 1% by weight, and preferably up to about 0.6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'indigotindisulfonic acid. Similarly, the dye known as F.D. & C. Green No. I, comprises a triphenylmethane dye and is the monosodium salt of 4-[4-Nethyl-p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857–884, which text is accordingly incorporated herein by reference.

Suitable oils and fats that are useable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

The quantity of adsorbate used may vary widely depending upon the particular medicament drug dosage. Amounts of medicament of about 1.0 to about 400 mg per medicated dosage are useable dependant upon the particular medicament. Naturally amounts of medicament adsorbate used will be higher depending on the therapeutic dosage required and amount of medicament adsorbed on the substrate. Illustrative examples are described below.

The usual dosage of diphenhydramine hydrochloride is between 10 and 50 mg per tablet. Incorporation of the adsorbate into, for example, a candy base is not difficult because of its melting point and solvent solubility. It is compatible with most flavors and is stable over a wide pH range. The diphenhydramine hydrochloride when added as the medicament adsorbate avoids its bitter taste and flavoring difficulty.

The usual dosage of phenidamine tartrate is about 10 to 50 mg per tablet. The formulation is not difficult to flavor because of the absence of medicament after-taste. The usual dosage of pyrilamine maleate is 25 to 50 mg per tablet. The usual dosage range of chlorpheniramine maleate is 2 to 4 mg and lends itself easily to incorporation into a candy base. Naturally, the exact amount used will vary with the particular application and drug.

The medicament adsorbate is generally present with the pharmaceutically acceptable carrier in an amount of from about 1% to about 60% by weight of the final composition. The exact amount will be dependent upon the particular medicament and dosage required.

The present invention is further illustrated by the following examples. All parts and percentages in the examples and throughout the specification and claims are by weight unless otherwise indicated.

EXAMPLE 1

This example demonstrates a method for preparing a dextromethorphan hydrobromide adsorbate.

To 120 kgs water is mixed 12 kgs dextromethorphan hydrobromide, at a water temperature around 90° C., until the drug was in solution. The solution was added to 35 kgs corn syrup (EMDEX®) and 91 kgs magnesium trisilicate having a mean specific surface area of 506.1 m²/g and mixed until a homogenous dispersion resulted, approximately 20 minutes. The mix was then oven dried at 70° C. until a moisture content of below 10% was obtained. The product was then milled to prepare a white free-flowing powder containing 8.0% by weight dextromethorphan hydrobromide.

An organoleptic evaluation test was performed on the product to determine the presence or absence of bitterness. The instant product did not exhibit any bitterness or off taste when tested by a human panel of experts.

EXAMPLE 2

This example demonstrates a method for preparing a pseudoephedrine adsorbate.

| | | |
|---|---|---|
| Silicon Dioxide (CABOSIL M5 ®) | 20.0% | 200 g |
| Magnesium Trisilicate | 40.0% | 400 g |
| Pseudoephedrine HCl(PSE) | 20.0% | 200 g |
| Polyvinylpyrrolidone (PVP) | 5.0% | 50 g |
| Corn starch | 15.0% | 150 g |
| | 100.0% | 1000 g |

Dissolve the PSE in 500 g of water. Charge the magnesium trisilicate (MTS) and silicon dioxide (SiO2) into a high shear mixer. Add the drug solution to the MTS/SiO2 by spraying at a rate of 100 cc/min and while mixing at 25 RPM main impeller). After the addition of the drug solution, add in the PVP and corn starch. Mix at 75 RPM (with main impeller and chopper at approximately 100 RPM. Mix until a uniform coarse granulation is produced. Discharge into a fluid bed drier and dry until the final moisture is between 2–10%. Mill using a Comil equipped with a 0.45" round holed grater screen at approximately 150 RPM.

EXAMPLE 3

This example demonstrates a method for preparing a multi-symptom adsorbate.

| | | |
|---|---|---|
| Magnesium Trisilicate (MTS) | 76% | 760 g* |
| Pyrilamine Maleate (PM) | 5% | 50 g |
| Dextromethorphan HBr (DM) | 3% | 30 g |
| Pseudoephedrine HCl (PSE) | 6% | 60 g |
| Hydroxypropylmethylcellulose (HPMC) | 5% | 50 g |
| Avicel PH 101 | 4% | 40 g |
| Poloxamer 407 | 1% | 10 g |
| | 100% | 1000 g |

Dissolve the PM, DM, PSE and Poloxamer 407 in 750 ml of hot water. Charge a low shear mixer, such as a hobart planetary mixer, with 760 g of MTS (based as anhydrous). This is done to adjust for the varying level of moisture contained in each lot of MTS. For example, if the MTS contained 20% moisture, a 20% excess of MTS would be added. Spray the drug solution onto the mixing MTS until done. Add in the Avicel and HPMC and mix until uniform. Additional water may be added to achieve the desired consistency. Discharge the mixer and dry the adsorbate at 70° C. in a forced hot air oven until a final moisture of 3% is reached. Mill the adsorbate using a Fitz Mill with impacts forward, at 2500 RPM with a 0 screen.

EXAMPLE 4

This example demonstrates a method for preparing various tablet formulations using one or more types of adsorbates prepared in a manner similar to Examples 1–3.

The following ingredients are mixed in the order indicated:

Composition of Cold Chewable Tablets Containing 30 mg of Pseudoephedrine HCl adsorbate.

| | | |
|---|---|---|
| Pseudoephedrine (PSE) adsorbate 18% w/w of PSE | 23.8% | 166.6 mg |
| Di-Pac (Compressible sugar) | 60.0% | 420.0 mg |
| Mannitol | 11.2% | 78.4 mg |
| Cherry flavor | 1.5% | 10.5 mg |
| Malic Acid | 0.5% | 3.5 mg |
| Adipic Acid | 1.0% | 7.0 mg |
| Magnesium Stearate | 0.5% | 3.5 mg |
| Aspartame | 1.5% | 10.5 mg |
| | 100.0% | 700 mg |

Composition of Multi-symptom Chewable Table Containing 15 mg Detromethorphan HBr, 30 mg of Pseudoephedrine HCl, 25 mg of Pyrilamine Maleate

| | | |
|---|---|---|
| Multisympton Adsorbate | 62.5% | 500 mg |
| Mannitol | 31.67% | 253.36 mg |
| Zinc stearate | 0.75% | 6 mg |
| Orange flavor | 2.0% | 16 mg |
| Citric acid | 2.0% | 16 mg |
| Sodium Saccharin | 0.08% | 0.64 mg |
| Aspartame | 1.0% | 8.0 mg |
| | 100% | 800 mg |

In the above example, 500 mg of acetaminophen can also be added to each tablet for fever and pain relief. This could be done by removing the mannitol and adding the acetaminophen. The chewable tablet weight would then be 1047 mg.

Composition of Cold/sinus/asthma Tablet Containing 4 mg Chlorpheniramine Maleate, 60 mg Pseudoephedrine HCl

| | |
|---|---|
| 1. Chlorpheniramine maleate (CPM) 10% adsorbate (4.0 mg drug/tablet) | 40 mg |
| 2. Pseudoephedrine HCI 10% adsorbate (60.0 mg drug/tablet) | 600 mg |
| 3. Microcrystalline cellulose | 50 mg |
| 4. Lactose | 75 mg |
| 5. Modified cellulose gum | 20 mg |
| 6. Fumed silica | 3 mg |
| 7. Stearic acid | 3 mg |
| 8. Magnesium stearate | 2 mg |
| | 793 mg |

Charge the microcrystalline cellulose, lactose, and modified cellulose gum into a twin-shell mixing blender. Mix for 5 minutes. Add in the CPM and PSE adsorbates and mix for 10 minutes. Add in the stearic acid and fumed silica and mix for 7 minutes. Add in the magnesium stearate and mix for 4 minutes.

The same mixing order would follow for a Bin blender, however, the mixing times would be 1.5 times longer than the above mixing times. This is because the bin method is less efficient.

EXAMPLE 5

A comparison was made between the blend sample lots of the medicament adsorbates of the present invention and those known prior to the date of this invention. Several blend sample lots of diphenhydramine hydrochloride adsorbates having a mean particle size greater than 100 um, and several blend sample lots of diphenhydramine hydrochloride adsorbates having a particle size no greater than about 40 um were subjected to analytical testing. The blends were sampled from ten points of a 50 cubic foot PK blender using the following sampling plan.

A blender was charged with final powder blends of the medicament adsorbates. The blender was started. After 5 minutes of mixing the blender was stopped. Samples were taken from ten different locations within the blender as shown below. Back-up samples were also taken in case retesting was necessary (a total of 20 samples were taken at the 5 minute interval).

The blender was closed and mixing began again for another 5 minutes. (This is now the 10 minute samples reported in Table 1). Ten samples were taken again with the appropriate back-ups. This procedure was repeated four more time (a total of 30 minutes of 30 minutes of mixing). In general, complete mixing of most powders occurrs between 15 and 30 minutes of mixing time.

Samples from the Blender (50 Cubic Foot PK Blender)—10 Locations

| | | |
|---|---|---|
| 1. | Top Left | |
| 2. | Top Left Center | |
| 3. | Top Right Center | |
| 4. | Top Right | TL, TLC, TRC, TR |
| 5. | Middle Left | ML, MM, MR |
| 6. | Middle Middle | BL, BR |
| 7. | Middle Right | DP |
| 8. | Bottom Left | |
| 9. | Bottom Right | |
| 10. | Discharge Port | |

NOTE: Approximately 750 mg +/−185 mg (single tablet weight) of blend was sampled (using a thief) in triplicate from each location in the blender. These samples were transferred separately into glass screw-cap vials. A single sample from each location was tested and the remaining two retained for further testing if required.

Table 1 shows the results of the blend studies which pertain to the diphenhydramine hydrochloride adsorbates having a particle size greater than about 100 um. The data shows uniformity at all test points for all the lots. The variability between the concentration of diphenhydramine hydrochloride at the different test points was about 1.5 to 2.5%. This variability is acceptable by current USP standards which requires a variability of no greater than 4%.

TABLE 1

| Blender Location | Sample Lot A | Sample Lot B | Sample Lot C | Sample Lot D |
|---|---|---|---|---|
| Top Left | 12.5 | 12.5 | 12.4 | 12.6 |
| Top Left Center | 12.5 | 12.7 | 12.8 | 13.0 |
| Top Right Center | 12.4 | 12.4 | 12.6 | 12.6 |
| Top Right | 12.7 | 12.2 | 12.6 | 12.8 |
| Middle Left | 12.6 | 12.4 | 13.0 | 13.1 |
| Middle Middle | 12.8 | 12.6 | 12.7 | 13.0 |
| Middle Right | 12.5 | 12.4 | 12.5 | 12.6 |
| Bottom Left | 12.4 | 12.6 | 12.1 | 13.0 |
| Bottom | 12.4 | 12.4 | 12.1 | 13.6 |

TABLE 1-continued

| Blender Location | Sample Lot A | Sample Lot B | Sample Lot C | Sample Lot D |
|---|---|---|---|---|
| Right Discharge Port | 12.2 | 12.3 | 11.8 | 13.6 |
| Average | 12.5 | 12.5 | 12.5 | 13.0 |
| % RSD | 1.36 | 1.21 | 2.93 | 2.87 |

Table 2 shows the results of the blend studies which pertain to the diphenhydramine hydrochloride adsorbates having a particle size no greater than about 40 um.

The samples show a high degree of drug variability. This is due to the fine, electrostatic adsorbate particles which will easily segregate. Upon segregation, two phenomena can occur, 1) the adsorbate forms agglomerates which collect at the surface of the powder and, 2) the fine adsorbate particles can sift through the blend and concentrate at the bottom of the blender.

The data shows a significant degree in variation in the amounts of adsorbates at all test points for the two lots, and thus fails to meet the specification stated in the process validation protocol. The variability between the concentration of diphenhydramine hydrochloride at the different test points was about 10% and with this high degree of variability, tablets would be cut of specification. Generally, a blend RSD greater than 4% produce poor quality tablets which will fail testing for potency and content uniformity.

TABLE 2

| Time Minutes | Sample Lot E | | | | | | |
|---|---|---|---|---|---|---|---|
| | Top Left | Top Middle | Top Right | Center Left | Center Right | Bottom Middle | Average % RSD |
| 15 | 12.61 | 12.28 | 11.44 | 13.38 | 12.44 | 16.41 | 13.09 |
| | | | | | | | 13.3 |
| 20 | 12.37 | 12.74 | 11.60 | 13.10 | 12.91 | 13.16 | 12.65 |
| | | | | | | | 4.63 |
| 25 | 12.67 | 12.40 | 11.83 | 13.10 | 12.26 | 13.42 | 12.62 |
| | | | | | | | 4.56 |
| 30 | 12.35 | 12.84 | 12.88 | 13.93 | 13.40 | 13.01 | 13.07 |
| | | | | | | | 4.13 |
| Final | 12.41 | 12.09 | 12.67 | 13.75 | 12.93 | 12.90 | 12.79 |
| | | | | | | | 4.43 |
| Average % RSD | 12.48 1.18 | 12.47 2.52 | 12.08 5.38 | 13.45 0.38 | 12.79 3.52 | 13.78 10.7 | |

EXAMPLE 6

A dissolution rate profile of the medicament adsorbate of the present invention (MA) was conducted to verify the release of diphenhydramine HCl. A dissolution (in-vitro) model was utilized to compare the medicament adsorbates versus known adsorbates (KA). Six tablets containing the medicament adsorbates were tested versus known adsorbates. The dissolution conditions were Apparatus 1 (baskets), 900 ml 0.1N HCl at a speed of 150 rpm. Samples were taken at 30, 45, 60, and 90 minutes neutralized and tested.

As shown in Table A, the tablets containing medicament adsorbates had a much better dissolution profile compared to the tablets containing known adsorbates. Also, it was observed that tablets containing medicament adsorbates completely disintegrated in less than 30 minutes whereas a portion of the tablets containing known adsorbates remained for even after 90 minutes.

As per USP requirements, dissolution testing of the two types of tablets for 45 minutes using 500 ml of deionized water with the basket apparatus at 100 RPM was conducted (Table B). In comparison, here again the tablets containing medicament adsorbates had faster dissolution than tablets containing known adsorbates.

TABLE A

| % DIPHENHYDRAMINE HCl RELEASED* | | | | |
|---|---|---|---|---|
| Adsorbate | 30 Minutes | 45 Minutes | 60 Minutes | 90 Minutes |
| MA | 93.1 | 99.3 | 101 | 101 |
| % RSD | 2.04 | 1.69 | 0.70 | 2.29 |
| KA | 37.2 | 51.2 | 60.2 | 71.5 |
| % RSD | 9.86 | 10.1 | 8.51 | 4.32 |

*Average of six tablets

TABLE B

| % DIPHENHYDRAMINE HCl RELEASED* | |
|---|---|
| Adsorbate | 45 Minutes |
| MA | 26.3 |
| % RSD | 6.91 |
| KA | 5.15 |
| % RSD | 13.6 |

*Average of six tablets

The invention being thus described, it will be obvious that the same may be varied in many ways. Such variations are not to be regarded as a departure from the spirit and scope of the invention and all such modifications are intended to be included within the scope of the following claims.

What is claimed is:

1. A medicament adsorbate which comprises an effective amount of a binder to reduce the electrostatic forces of the adsorbate and containing adsorbed therein from about 10% to about 90% by weight of the adsorbate magnesium trisilicate wherein the magnesium trisilicate has a surface area of at least 400 $m^2/g$ and a structure with multiple interstitial spaces and containing adsorbed therein from about 0.5% to about 30% by weight of the adsorbate of a medicament drug, the medicament adsorbate being of a size characterized by a density in the range from about 700 to about 1000 grams/liter.

2. The adsorbate of claim 1 wherein the binder is an alkyl cellulose derivative selected from the group consisting of ethylcellulose, hydroxypropylcellulose, hydroxypropylmethylcellulose, methylcellulose and sodium carboxymethylcellulose and mixtures thereof.

3. The adsorbate of claim 1 wherein the medicament drug is an antihistamine.

4. The adsorbate of claim 1 wherein the medicament drug is selected from the group of antihistamine materials consisting of chlorpheniramine maleate, phenindamine tartrate, pyrilamine maleate, doxylamine succinate, phenyltoloxamine citrate, diphenhydramine hydrochloride, promethazine, triprolidine, and mixtures thereof.

5. The adsorbate of claim 1 wherein the binder is present in the amount of about 0.5 to about 60% by weight of the adsorbate.

6. The adsorbate of claim 1 wherein the medicament trisilicate has a surface area of about 440 $m^2/g$ to about 600 $m^2/g$.

7. The adsorbate of claim 1 wherein the binder is selected from the group consisting of corn syrup, PVP, starches, sugars, gelatin, and alkyl cellulose compounds.

8. The adsorbate of claim 1 wherein the binder is corn syrup.

9. The adsorbate of claim 1 wherein the adsorbate is combined with at least one pharmaceutically acceptable excipient.

10. The adsorbate of claim 1 wherein the adsorbate is part of a tablet.

11. The adsorbate of claim 1 wherein the adsorbate size is in the range greater than 40 to about 800 um.

12. The adsorbate of claim 1 wherein the adsorbate size is in the range greater than 150 to about 600 um.

13. A medicament adsorbate which consists essentially of from about 0.5 to about 60% by weight of the adsorbate a binder and magnesium trisilicate adsorbed therein from about 10 to about 90% by weight of the adsorbate wherein the magnesium trisilicate has a surface area of at least 400 $m^2/g$ and a structure with multiple interstitial spaces and containing adsorbed therein from about 0.5 to about 30% by weight of the adsorbate of diphenhydramine hydrochloride, the adsorbate being of a size in the range greater than 150 to about 600 um.

14. The adsorbate of claim 13 wherein the adsorbate has a density in the range from about 700 to about 1000 grams/liter.

15. The adsorbate of claim 14 wherein the binder is corn syrup and the amount of corn syrup is from about 3 to about 40% by weight of the adsorbate.

16. The adsorbate of claim 15 wherein the medicament drug is present in the amount of about 5 to about 20% by weight of the adsorbate.

17. The adsorbate of claim 16 wherein the medicament trisilicate has a surface area of about 440 $m^2/g$ to about 600 $m^2/g$.

18. The adsorbate of claim 17 wherein the adsorbate is combined with at least one pharmaceutically acceptable excipient.

19. A process for preparing a medicament adsorbate which comprises dissolving a medicament drug in solvent, admixing magnesium trisilicate wherein the magnesium trisilicate has a surface area of at least 400 $m^2/g$ and a structure with multiple interstitial spaces and admixing a binder to prepare a mass having a homogenous consistency to enable migration of the medicament drug within the intersistial spaces of the magnesium trisilicate, and recovering the medicament adsorbate product.

20. The adsorbate of claim 19 wherein the binder is an alkyl cellulose derivative selected from the group consisting of ethylcellulose, hydroxypropylcellulose, hydroxypropylmethylcellulose, methylcellulose and sodium carboxymethylcellulose and mixtures thereof.

21. The process of claim 19 which comprises employing about 5 to about 40% by weight solvent to prepare a granulated admixture containing the medicament drug, binder and magnesium trisilicate adsorbate which is dried to a final moisture content of about 1 to about 25% weight.

22. The process of claim 21 which comprises employing about 40 to about 80% by weight solvent to prepare a slurry and thereafter removing the solvent from the slurry to form a paste.

23. The process of claim 22 wherein the paste is dried and recovered as a free flowing powder.

24. The process of claim 23 wherein a pharmaceutically acceptable carrier is added to the powder.

* * * * *